US00RE48426E

(19) United States
(12) Reissued Patent
Murray et al.

(10) Patent Number: US RE48,426 E
(45) **Date of Reissued Patent: *Feb. 9, 2021**

(54) PACKAGED READY-TO-USE PRODUCT

(71) Applicant: Hollister Incorporated, Libertyville, IL (US)

(72) Inventors: Michael Murray, Ballina (IE); Thomas H. Gilman, Spring Grove, IL (US); Sean Sweeney, Ballina (IE); Martin P. Creaven, Ballina (IE)

(73) Assignee: Hollister Incorporated, Libertyville, IL (US)

( * ) Notice: This patent is subject to a terminal disclaimer.

(21) Appl. No.: 16/421,115

(22) Filed: May 23, 2019

Related U.S. Patent Documents

Reissue of:
(64) Patent No.: 9,072,862
Issued: Jul. 7, 2015
Appl. No.: 14/249,568
Filed: Apr. 10, 2014

U.S. Applications:
(63) Continuation of application No. 15/438,220, filed on Feb. 21, 2017, now Pat. No. Re. 47,513, which is an
(Continued)

(51) Int. Cl.
*A61M 25/00* (2006.01)
*A61M 25/01* (2006.01)
(Continued)

(52) U.S. Cl.
CPC ..... *A61M 25/002* (2013.01); *A61M 25/0009* (2013.01); *A61M 25/0017* (2013.01);
(Continued)

(58) Field of Classification Search
CPC ..... A61M 25/002; A61M 25/0009; A61M 25/0017; A61M 25/0111; A61M 25/007;
(Continued)

(56) References Cited

U.S. PATENT DOCUMENTS 3,800 A 10/1844 Gale
2,915,063 A 12/1959 Cutter
(Continued)

FOREIGN PATENT DOCUMENTS

AU 706432 B2 6/1999
CN 1106744 A 8/1995
(Continued)

OTHER PUBLICATIONS

Third-Party observations submitted in EP Application No. EP 17150789.0 dated May 20, 2020.
(Continued)

*Primary Examiner* — Patricia L Engle
(74) *Attorney, Agent, or Firm* — Cook Alex Ltd.

(57) ABSTRACT

A vapor hydrated packaged catheter assembly and method of manufacturing and distributing same includes a gas impermeable package housing a catheter within a catheter-receiving cavity. The catheter assembly has a hydrophilic coating applied to at least a portion of the outer surface of a catheter tube or shaft which may be surrounded by a sleeve to provide a no-touch, sure grip feature. The catheter assembly is disposed within the catheter receiving cavity of the package together with a limited amount of a vapor donating liquid provided as a source of vapor to activate the hydrophilic coating. The amount of vapor donating liquid is less than the amount that would otherwise be sufficient to cause a spill hazard. It may be loose liquid as a desired percentage of the volume of a tube-receiving portion of the catheter receiving cavity of the package, or it may be contained in a liquid sequestering element. The activation of at least some of the hydrophilic coating occurs solely by reason of exposure of the outer surface of the catheter to a vapor produced by the vapor donating liquid. The distribution of the catheter following manufacture is delayed for a time sufficient to
(Continued)

permit the vapor to complete hydration of the entire hydrophilic coating on the surface.

20 Claims, 9 Drawing Sheets

Related U.S. Application Data application for the reissue of Pat. No. 9,072,862, which is a continuation of application No. 13/480,669, filed on May 25, 2012, now Pat. No. 8,720,685, which is a continuation of application No. 13/196,382, filed on Aug. 2, 2011, now Pat. No. 8,205,745, which is a continuation of application No. 12/098,046, filed on Apr. 4, 2008, now Pat. No. 8,011,505, which is a continuation of application No. 10/540,148, filed as application No. PCT/US2004/025417 on Aug. 6, 2004, now Pat. No. 7,380,658.

(60) Provisional application No. 60/493,493, filed on Aug. 8, 2003.

(51) Int. Cl.

| | |
|---|---|
| ***B65B 55/22*** | (2006.01) |
| ***B65B 5/04*** | (2006.01) |
| ***B65B 7/02*** | (2006.01) |
| ***B65D 81/22*** | (2006.01) |
| *A61M 25/06* | (2006.01) |

(52) U.S. Cl.
CPC ..... *A61M 25/0111* (2013.01); *B65B 5/04* (2013.01); *B65B 7/02* (2013.01); *B65B 55/22* (2013.01); *B65D 81/22* (2013.01); *A61M 25/007* (2013.01); *A61M 2025/0046* (2013.01); *A61M 2025/0681* (2013.01)

(58) Field of Classification Search
CPC ..... A61M 2025/00681; A61M 2025/0046; A61M 2025/0045; A61M 2025/0062; A61M 2025/0067; B65D 81/22; B65B 55/22; B65B 5/04; B65B 7/02
See application file for complete search history.

(56) References Cited

U.S. PATENT DOCUMENTS

| | | | |
|---|---|---|---|
| 2,947,415 | A | 8/1960 | Garth |
| 3,035,691 | A | 5/1962 | Rasmussen et al. |
| 3,286,832 | A | 11/1966 | Pilger |
| 3,345,988 | A | 10/1967 | Vitello |
| 3,460,529 | A | 8/1969 | Leucci |
| 3,556,294 | A | 1/1971 | Walck et al. |
| 3,648,704 | A | 3/1972 | Jackson |
| 3,754,871 | A | 8/1973 | Hessel et al. |
| 3,854,483 | A | 12/1974 | Powers |
| 3,861,395 | A | 1/1975 | Taniguchi |
| 3,894,540 | A | 7/1975 | Bonner, Jr. |
| 3,898,993 | A | 8/1975 | Taniguchi |
| 3,930,580 | A | 1/1976 | Bazel et al. |
| 3,934,721 | A | 1/1976 | Juster et al. |
| 3,967,728 | A | 7/1976 | Gordon et al. |
| 4,026,296 | A | 5/1977 | Stoy et al. |
| 4,062,363 | A | 12/1977 | Bonner, Jr. |
| 4,116,338 | A | 9/1978 | Weichselbaum |
| 4,119,094 | A | 10/1978 | Micklus et al. |
| 4,170,996 | A | 10/1979 | Wu et al. |
| 4,204,527 | A | 5/1980 | Wu et al. |
| 4,230,115 | A | 10/1980 | Walz, Jr. et al. |
| 4,269,310 | A | 5/1981 | Uson |
| 4,379,506 | A | 4/1983 | Davidson |
| 4,497,402 | A | 2/1985 | Karos |
| 4,623,329 | A | 11/1986 | Drobish et al. |
| 4,652,259 | A | 3/1987 | O'Neil |
| 4,692,154 | A | 9/1987 | Singery |
| 4,811,847 | A | 3/1989 | Reif et al. |
| 4,863,016 | A | 9/1989 | Fong et al. |
| 4,906,237 | A | 3/1990 | Johansson et al. |
| 4,925,448 | A | 5/1990 | Bazaral |
| 5,147,341 | A | 9/1992 | Starke et al. |
| 5,180,591 | A | 1/1993 | Magruder et al. |
| 5,226,530 | A | 7/1993 | Golden |
| 5,242,398 | A | 9/1993 | Knoll et al. |
| 5,242,428 | A | 9/1993 | Palestrant |
| 5,334,166 | A | 8/1994 | Palestrant |
| 5,348,678 | A | 9/1994 | Hodam, Jr. et al. |
| 5,416,131 | A | 5/1995 | Wolff et al. |
| 5,454,798 | A | 10/1995 | Kubalak et al. |
| 5,582,165 | A | 12/1996 | Bryan |
| 5,645,527 | A | 7/1997 | Beck |
| 5,660,868 | A | 8/1997 | Yeager |
| 5,688,459 | A | 11/1997 | Mao et al. |
| 5,800,412 | A | 9/1998 | Zhang et al. |
| 5,871,091 | A | 2/1999 | Fogle |
| 5,938,012 | A | 8/1999 | Yeager et al. |
| 5,968,069 | A | 10/1999 | Dusbabek et al. |
| 6,004,305 | A | 12/1999 | Hursman et al. |
| 6,053,905 | A | 4/2000 | Daignault, Jr. et al. |
| 6,059,107 | A | 5/2000 | Nosted et al. |
| 6,090,075 | A | 7/2000 | House |
| 6,119,855 | A | 9/2000 | Yeager et al. |
| 6,123,712 | A | 9/2000 | Di Caprio et al. |
| 6,159,227 | A | 12/2000 | Di Caprio et al. |
| 6,355,004 | B1 | 3/2002 | Pedersen et al. |
| 6,391,010 | B1 | 5/2002 | Wilcox |
| 6,403,759 | B2 | 6/2002 | Stamler et al. |
| 6,409,717 | B1 | 6/2002 | Israelsson et al. |
| 6,506,201 | B2 | 1/2003 | Di Caprio et al. |
| 6,578,709 | B1 | 6/2003 | Kavanagh et al. |
| 6,602,244 | B2 | 8/2003 | Kavanagh et al. |
| 6,634,498 | B2 | 10/2003 | Kayerod et al. |
| 6,736,805 | B2 | 5/2004 | Israelsson et al. |
| 6,848,574 | B1 | 2/2005 | Israelsson et al. |
| 6,877,601 | B1 | 4/2005 | Colombo |
| 6,887,230 | B2 | 5/2005 | Kubalak et al. |
| 6,996,952 | B2 | 2/2006 | Gupta et al. |
| 7,066,912 | B2 | 6/2006 | Nestenborg et al. |
| 7,087,048 | B2 | 8/2006 | Israelsson et al. |
| 7,234,597 | B2 | 6/2007 | Rowe et al. |
| 7,311,698 | B2 | 12/2007 | Tanghoj et al. |
| 7,380,658 | B2 | 6/2008 | Murray et al. |
| 7,476,223 | B2 | 1/2009 | McBride |
| 7,615,045 | B2 | 11/2009 | Israelsson et al. |
| 7,631,760 | B2 | 12/2009 | Guelzow et al. |
| 7,770,726 | B2 | 8/2010 | Murray et al. |
| 7,886,907 | B2 | 2/2011 | Murray et al. |
| 8,011,505 | B2 | 9/2011 | Murray et al. |
| 8,740,863 | B2 * | 6/2014 | Nestenborg et al. ..... 604/265 |
| 2001/0001443 | A1 | 5/2001 | Kayerod et al. |
| 2001/0054562 | A1 | 12/2001 | Pettersson et al. |
| 2002/0068180 | A1 | 6/2002 | Yang et al. |
| 2002/0103467 | A1 | 8/2002 | Kubalak |
| 2003/0018322 | A1 | 1/2003 | Tanghoj et al. |
| 2003/0168365 | A1 | 9/2003 | Kaern |
| 2003/0229374 | A1 | 12/2003 | Brady et al. |
| 2004/0074794 | A1 | 4/2004 | Conway et al. |
| 2004/0153051 | A1 | 8/2004 | Israelsson et al. |
| 2005/0015076 | A1 | 1/2005 | Giebmeyer et al. |
| 2005/0033311 | A1 | 2/2005 | Guldfeldt |
| 2005/0049577 | A1 | 3/2005 | Snell |
| 2005/0070882 | A1 | 3/2005 | McBride |
| 2005/0137582 | A1 | 6/2005 | Kull-Osterlin et al. |
| 2006/0163097 | A1 | 7/2006 | Murray et al. |
| 2007/0088330 | A1 | 4/2007 | House |
| 2007/0161971 | A1 | 7/2007 | House |
| 2007/0289887 | A1 | 12/2007 | Murray et al. |
| 2008/0272012 | A1 | 11/2008 | Stopek |
| 2009/0099532 | A1 | 4/2009 | Cuevas et al. |
| 2009/0131917 | A1 | 5/2009 | Kavanagh et al. |
| 2009/0200186 | A1 * | 8/2009 | Nestenborg et al. ..... 206/364 |

(56) References Cited

U.S. PATENT DOCUMENTS

| | | | | |
|---|---|---|---|---|
| 2009/0200187 | A1* | 8/2009 | Nestenborg et al. | 206/364 |
| 2009/0299334 | A1 | 12/2009 | Nishtala | |
| 2010/0264050 | A1 | 10/2010 | Clarke et al. | |

FOREIGN PATENT DOCUMENTS

| | | | |
|---|---|---|---|
| CZ | 197409 | | 8/1979 |
| DE | 2317839 | A1 | 10/1974 |
| DK | 1023/96 | C | 8/1965 |
| DK | 1023/960 | C | 8/1965 |
| DK | 1224/96 | A | 3/1998 |
| EP | 0217771 | A1 | 4/1987 |
| EP | 0348840 | B1 | 1/1990 |
| EP | 0586324 | A1 | 3/1994 |
| EP | 0677299 | A1 | 10/1995 |
| EP | 0680895 | A1 | 11/1995 |
| EP | 0685179 | B1 | 12/1995 |
| EP | 0815037 | A1 | 1/1998 |
| EP | 0923398 | A1 | 6/1999 |
| EP | 0959930 | A1 | 12/1999 |
| EP | 1115450 | A1 | 7/2001 |
| EP | 1115450 | B1 | 7/2001 |
| EP | 1145729 | A1 | 10/2001 |
| EP | 1642610 | A2 | 4/2006 |
| EP | 1642611 | A2 | 4/2006 |
| EP | 1642611 | B1 | 4/2006 |
| EP | 1647298 | A2 | 4/2006 |
| EP | 1809345 | B1 | 7/2007 |
| EP | 1420846 | B1 | 12/2010 |
| GB | 1600963 | A | 10/1981 |
| GB | 2284764 | A | 6/1995 |
| GB | 2334315 | A | 8/1999 |
| JP | 49-132888 | U | 11/1974 |
| JP | S49-132888 | U | 11/1974 |
| JP | 55-12265 | | 12/1974 |
| JP | 55 012265 | A | 1/1980 |
| JP | SHO 55-012265 | A | 3/1980 |
| JP | 2001-139059 | | 5/2001 |
| JP | 2001/1399059 | A1 | 5/2001 |
| SE | 9600276-1 | | 1/1996 |
| WO | WO 86/06284 | A1 | 11/1986 |
| WO | WO 93/03777 | A1 | 3/1993 |
| WO | WO 94/06377 | A1 | 3/1994 |
| WO | WO 94/16747 | A1 | 8/1994 |
| WO | WO 96/30277 | A1 | 10/1996 |
| WO | WO 97/26937 | A1 | 7/1997 |
| WO | WO 97/39697 | A1 | 10/1997 |
| WO | WO 98/11932 | A1 | 3/1998 |
| WO | WO 98/19729 | A1 | 5/1998 |
| WO | WO 98/41116 | A1 | 9/1998 |
| WO | WO 98/58988 | A1 | 12/1998 |
| WO | WO 99/30761 | A1 | 6/1999 |
| WO | WO 99/42155 | A2 | 8/1999 |
| WO | WO 00/16843 | A1 | 3/2000 |
| WO | WO 00/30696 | A1 | 6/2000 |
| WO | WO 00/47494 | A1 | 8/2000 |
| WO | WO 01/52763 | A1 | 7/2001 |
| WO | WO 03/008029 | A2 | 1/2003 |
| WO | WO 03/093357 | A1 | 11/2003 |
| WO | WO 04/056909 | A1 | 7/2004 |
| WO | WO 2005/004970 | A1 | 1/2005 |
| WO | WO 2005/014055 | A2 | 2/2005 |
| WO | WO 2006/037321 | A1 | 4/2006 |

OTHER PUBLICATIONS

Third-Party observations submitted in EP Application No. EP 17205430.6 dated May 20, 2020.

European Patent Official pursuant to Article 94(3) EPC issued in EP Application No. EP 17150789.0 on Oct. 29, 2019.

Communication of Notice of Opposition in EP 2423125, issued by the EPO on Apr. 4, 2019 and Opposition Against European patent No. EP 2423125.

Medical Device Packaging Handbook, edited by Max Sherman, Second Edition 1998, table of contents and pp. 76-89.

JP Office Action dated Jan. 22, 2010 as received in Application No. 2006-522746.

JP Decision to Grant dated Jan. 28, 2011 as received in Application No. 2006-522746.

JP Decision to Grant dated May 7, 2012 as received in Application No. 2010-167138.

Extended European Search Report for Application No. 17205430.6 dated Sep. 26, 2018.

European Office Action dated Jul. 13, 2009 for European Patent Application No. 1606196.

European Office Action dated Feb. 16, 2010 for European Patent Application No. 1606196.

Observations by third parties dated Nov. 1, 2010 for European Patent Application No. 1606196.

Observations by third parties dated Jan. 18, 2011 for European Patent Application No. 1606196.

Transmittal of third party dated Jan. 24, 2011 for European Patent Application No. 1606196.

European Office Action dated May 22, 2014 for European Patent Application No. EP 2423125.

Decision of Board of Appeals dated Mar. 23, 2012 for European Patent Application No. EP 2423125.

Decision of Board of Appeals dated Jul. 7, 2009 for European Patent Application No. EP 2423125.

Third Party Observations dated Jun. 7, 2016 for European Patent Application No. EP 2423125.

Observations of Third Parties dated Jun. 7, 2016 for European Patent Application No. EP 2423125.

European Office Action dated Jul. 18, 2016 for European Patent Application No. EP 2423125.

Observations of Third Parties dated Sep. 12, 2016 for European Patent Application No. EP 2423125.

Non-patent literature cited during opposition procedure for EP2423126: Polymer Foams, 3.063 Polymer Physics, Spring 2007, Katrine Sivertsen.

Non-patent literature cited during opposition procedure for EP 2423126: Handbook of Polymer Foams, Editor David Eaves, Rapra Technology Limited, 2004, ISBN: 1-85957-388-6.

Non-patent literature cited during opposition procedure for EP2423126: Medical Device Packaging Handbook, edited by Joseph D. O'Brien, Packaging and Converting Technology, 1991, pp. 86-90, 118-122, and 139-140.

Non-patent literature cited during opposition procedure for EP2423126, on Dec. 29, 2016: Wikipedia—Foam.

Notice of Opposition dated Jan. 11, 2017 for EP2423126.

Extended European Search Report dated Aug. 2, 2017, for application No. EP17150789.0-1664/3210909.

EPO Office Action dated Jul. 13, 2009 for Application No. 04 780 281.4.2320.

Decision of the Board of Appeal Jul. 7, 2009 for Application No. 97901879.3.

Ikada et al., "Lubricating Polymer Surfaces," Research Center for Biomedical Engineering, Kyoto University, pp. 58-60 (1993).

Tidd et al., "Comparison of Hydrophilic Polymer-Coated Latex, Uncoated Latex and PVC Indwelling Balloon Catheters in the Prevention of Urinary Infection," British Journal of Urology, 48:285-291 (1976).

European Search Report for Application No. EP 11150060.9, dated Mar. 8, 2011.

European Search Report for Application No. EP 11150068.2, dated Mar. 7, 2011.

International Search Report for Application No. PCT/US04/25414, dated Feb. 9, 2005.

EPO Office Action dated May 22, 2014 for Application No. EP 11175010.5.

EPO Office Action dated May 22, 2014 for Application No. EP 11175017.0.

European Search Report for EP Application No. 11175010.5 (EP Publication No. 2423125) dated Jan. 26, 2012.

EPO Office Action for EP Application No. 11175010.5 (EP Publication No. 2423125) dated May 22, 2014.

(56) References Cited

OTHER PUBLICATIONS

Third Party Observations for EP Application No. 11175010.5 (EP Publication No. 2423125) dated Jun. 7, 2016.
EPO Office Action for EP Application No. 11175010.5 (EP Publication No. 2423125) dated Jul. 18, 2016.
Third Party Observations for EP Application No. 11175010.5 (EP Publication No. 2423125) dated Sep. 12, 2016.
European Search Report for EP Application No. 11175016.2 (EP Publication No. 2423126) dated Jan. 26, 2012.
Notice of Opposition for EP Application No. 11175016.2 (EP Publication No. 2423126) dated Dec. 29, 2016.
Notice of Opposition for EP Application No. 11175016.2 (EP Publication No. 2423126) dated Jan. 11, 2017.
Notice of Opposition for EP Application No. 11175016.2 (EP Publication No. 2423126) dated Feb. 7, 2017.
European Search Report for EP Application No. 11175017.0 (EP Publication No. 2423127) dated Jan. 26, 2012.
EPO Office Action for EP Application No. 11175017.0 (EP Publication No. 2423127) dated May 22, 2014.
EPO Office Action for EP Application No. 11175017.0 (EP Publication No. 2423127) dated Aug. 26, 2016.
English translation and Danish version of "Writ of Summons", Plaintiff: Coloplast A/S, Defendant: Hollister Incorporated, Copenhagen, Jan. 6, 2017, Kromann Reumert, Nicolai Lindgreen.
Notice of Opposition to EP 1606196, dated Dec. 11, 2012, by Opponent Coloplast A/S.
Response to Opposition, in reference to the EPO Letter dated Jan. 22, 2013, dated May 31, 2013.
EPO Office Action dated Jul. 13, 2009 for App. No. 04 780 281.4.2320.
Decision of the Board of Appeal Jul. 7, 2009 for App. No. 97901879.3.
Supplementary European Search Report for PCT US2004025417 dated Feb. 25, 2009.
Third-Party observations submitted in EP Application No. EP 04780281.4 dated Nov. 1, 2010.
Third-Party observations submitted in EP Application No. EP 04780281.4 dated Jan. 18, 2011.
"LoFric: The Leading Low Friction, Low Risk Catheter," Astra Tech (2006).
"The LoFric Story," Astra Tech (2006).
Ikeda et al., "Lubricating Polymer Surfaces," Research Center for Biomedical Engineering, Kyoto University, pp. 58-60 (1993).
Kelly et al., "Prolonging the Life of the Hydrophilic-Conted Catheter," British Journal of Urology, 79 (Suppl 4): 12 (1997).
Moore, "Intermittent Self-Catheterisation; Research-Based Practice," British Journal of Nursing, 4(18):1057 (1995).
O'Neil, "At last: A System Which Addresses All the Issues of Nosocomial U.T.I. Associated with Catherization," Nursing Times, 33:88-90 (1986).
Written Opinion for Application No. PCT/US04/25417, dated Feb. 9, 2005.
EPO Office Action dated May 5, 2014 for App. No. EP 11175010.5.
EPO Office Action dated May 5, 2014 for App. No. EP 11175017.0.

* cited by examiner

PACKAGED READY-TO-USE PRODUCT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

This application is a *continuation reissue application of U.S. patent application Ser. No. 15/438,220, filed Feb. 21, 2017, which is an application for reissue of U.S. Pat. No. 9,072,862, now Re 47,513 issued Jul. 16, 2019, which issued from U.S. patent application Ser. No. 14/249,568, filed Apr. 10, 2014, which was a* continuation application of U.S. patent application Ser. No. 13/480,669, filed May 25, 2012, *now U.S. Pat. No. 8,720,685,* which was a continuation application of U.S. patent application Ser. No. 13/196,382, filed Aug. 2, 2011, now U.S. Pat. No. 8,205,745, which was a continuation application of U.S. patent application Ser. No. 12/098,046, filed Apr. 4, 2008, now U.S. Pat. No. 8,011,505, which was a continuation of U.S. patent application Ser. No. 10/540,148, filed Dec. 5, 2005, now U.S. Pat. No. 7,380,658, which was a U.S. National Stage of PCT Application No. PCT/US04/025417, filed Aug. 6, 2004, which claims priority to U.S. Provisional Patent Application No. 60/493,493, filed Aug. 8, 2003, all of the above of which are hereby incorporated herein by reference. *Notice: more than one reissue application has been filed for the reissue of U.S. Pat. No. 9,072,862. The reissue applications are application Ser. Nos. 15/438,220 and 16/421,115* (*this application*).

BACKGROUND

Intermittent catheterization is a good option for many users who suffer from various abnormalities of the urinary system. A common situation is where single use, individually packaged, sterile catheters are used. An important criterion for any single use product is the cost of the product, i.e., a less expensive product is desired and valued.

It is also quite common for catheters to be provided with a surface treatment using a lubricant to reduce friction in order to allow for easier and less traumatic insertion. Currently, there are two major categories of catheters having lubricated surfaces, i.e., gel coated catheters and hydrophilic coated catheters.

The gel coated catheters are made easier to insert by application to the catheter surface of a water-based gel that can be applied by the user, or more conveniently, it can be supplied with the packaged catheter. Typically, a system is provided with the packaged catheter to apply the gel to the catheter surface. This system may be one where the gel is put onto the catheter surface just before or during the packaging operation or one where the gel is applied to the surface as the catheter is being inserted by the user.

In a hydrophilic coated catheter, the catheter is provided with a thin hydrophilic coating which is adhered to the outer surface of the catheter. When this coating is activated by swelling in contact with a hydrating liquid such as water, it becomes an extremely low coefficient of friction surface. The most common form of this product is where a sterile, individually packaged single use catheter is provided in a dry state or condition. The user opens the package, pours water into the package, waits 30 seconds, and then removes the catheter from the package, now ready for insertion.

A more recently introduced version of the hydrophilic coated catheter is where the catheter is provided in a package that already contains enough loose liquid water to cause it to be immersed. For this product, the user simply opens the package and removes the catheter ready for insertion without the need to add water and wait 30 seconds. Other new products provide the amount of liquid water necessary for immersion of the catheter in a separate compartment of the package. With these products, one must open the separate compartment of the package allowing the liquid immersion water to enter the catheter-containing chamber for direct contact with the hydrophilic coated surface. Depending on the product, and on the amount of water in the separate chamber, the user may be asked to manipulate the package to bathe the catheter surface in the hydrating liquid in order to activate the hydrophilic coating on the catheter surface. The catheter is then removed from the package ready for insertion by the user.

In all of these existing products, the catheter depends upon direct contact of the liquid swelling medium (e.g., liquid water) with the entirety of the hydrophilic coated catheter surface. Moreover, all of these existing products achieve this direct liquid water contact by providing a package for the catheter that permits liquid water to flow freely within the cavity of the package, and permits unobstructed access to the catheter surface. Because of the free flow of loose liquid water within the package and unobstructed access to the catheter surface, it is easy to ensure direct contact of the liquid swelling medium with the entire surface of the catheter that has been treated with the hydrophilic coating.

A disadvantage of the hydrophilic coated catheters described above is that the immersion liquid has a tendency to spill from the package as the user handles the catheter and tries to remove it for subsequent insertion. Another disadvantage of the hydrophilic coated catheters described above is that the catheter has an extremely slippery surface which makes it quite difficult for the user to handle during insertion.

For catheters that are removed from the package and then inserted, there is another disadvantage in that the handling of the catheter by the user will introduce microorganisms onto the surface of the catheter which can cause infectious problems after being introduced into the body during catheter insertion. To address this issue, manufacturers have devised systems whereby the catheter can be inserted by the user without first removing the catheter from the package, thus requiring the user to touch only the package, and not the catheter surface. These systems tend to work well for gel coated catheters, and they have the additional advantage that the user does not get gel on his or her hands as the catheter is being inserted. Another version of the gel lubricated catheter utilizes a sleeve around the catheter which is attached to a gel reservoir at the insertion end of the catheter whereby the gel reservoir and sleeve come out of the package attached to the catheter which is inserted by advancing it through the gel reservoir. In this type of product, the sleeve fits the catheter diameter very loosely, thereby allowing the catheter and the integral funnel which is typically provided on the distal end of the catheter to slip past the sleeve surface as the catheter is advanced by the user during insertion.

For hydrophilic coated catheters, there has also been consideration of delivery of the catheter without first removing it from the package, but a serious problem for this type of approach is the tendency of the immersion liquid to spill. Hydrophilic coated catheters with sleeves of any kind have generally not been available, because the presence of the sleeve interferes with the flow of liquid water to the catheter surface that is required for activation by direct liquid contact. Some designs are described in the patent literature where the hydrating liquid is inside of a hose member that can be used as a no touch delivery vehicle (See, for example, United States Publication No. 2003/0018322 A1, published Jan. 23, 2003). These described hose members are stiff, though, and require special concertina folds to allow for advancement of the catheter, and special gripping sections to allow for gripping of the catheter.

In some of the published patent art, for example, U.S. Pat. No. 6,059,107, there is discussion of keeping low the amount of water placed in the package with the catheter. They propose to do this, however, by simultaneously providing a narrow cavity around the catheter tube thereby using the design of the cavity to accomplish a reduction in the amount of water. In this way, the catheter remains substantially immersed in and subject to direct liquid water contact while contained in the package.

In one commercial product, the cavity is not completely filled with water, and so recommendation is made to the user to tilt or otherwise manipulate the package prior to use, to ensure direct liquid water contact with the catheter in order to fully activate the hydrophilic surface coating. Similarly, some commercial products with a liquid reservoir that is to be ruptured prior to use do not have enough liquid water to fill the package cavity that holds the catheter. The user is instructed to tilt the package multiple times to cause liquid water to move over the catheter to activate the hydrophilic surface coating by direct liquid water contact. As mentioned above, the liquid water in the package cavity presents a spill hazard for the user when the package is opened to use the catheter. As will be appreciated, the spill hazard is greater for hydrophilic catheters that more completely fill the package cavity with liquid water, whereas more patient manipulation is required for hydrophilic catheters that fill the cavity less completely with liquid water.

There is a tradeoff, then, between undesirable alternatives with existing hydrophilic catheter products. On the one hand, the package cavity is provided with a quantity of liquid water designed to keep the catheter substantially immersed, but there is a significant spill hazard. On the other hand, when there is less liquid water relative to the overall package cavity volume, the user must manipulate the package prior to use to ensure activation of the catheter coating. The present invention avoids this tradeoff by eliminating any spill hazard while requiring no user manipulation.

SUMMARY OF THE INVENTION

The hydrophilic catheter of the present invention is vapor hydrated with a vapor swelling medium such as water vapor within the catheter package in such a manner that it is ready for use when it reaches the user with little or no possibility of liquid spillage. it results in a sterile catheter package that does not require the addition of an immersion liquid but, rather, already has the hydrophilic surface coating of the catheter activated by reason of vapor hydration. The catheter package may contain a liquid sequestering element such as fabric or foam sized to contain an amount of liquid that can produce sufficient vapor to form and maintain a vapor hydration atmosphere within the package cavity. The fabric or foam liquid sequestering element reliably holds liquid in its interstices to prevent loose liquid from presenting a spill hazard while permitting vapor to be formed and escape into the package cavity. The catheter package of the invention may also contain a thin, flexible sleeve of polymeric film fitting about the catheter tube. The flexible sleeve serves to make the very lubricious vapor hydrated catheter easier for the user to handle while also permitting sterile insertion into the body. This is due to the outer, handling portion of the flexible sleeve of the catheter being much less slippery than the outer surface of the catheter having the vapor hydrated hydrophilic surface coating. The sleeve can be made to closely fit the outer surface of the catheter tube, which will reduce the amount of material used for the sleeve and so lower its cost. A close fitting sleeve will also prevent or at least severely limit the extent of lateral movement of the catheter within the sleeve. The sleeve can also be made of a material that permits water vapor, but not liquid water, to penetrate, and this will speed the process of vapor activation of the coating.

In those embodiments having a sleeve within the package, the relatively small quantity of liquid introduced into the package during manufacture is located externally of the sleeve. Thus, the hydrophilic surface coating of the catheter tube is hydrated following manufacture, after the package is sealed, by vapor generated within the package during an extended and predetermined period of incubation or aging prior to catheter use. Accordingly, the catheter of the invention is provided in a cost effective, easy to manufacture manner that overcomes the problems heretofore encountered in providing a hydrophilic coated catheter that is ready for use. When very flexible, narrow sleeves are used, there is a further advantage in that the user can fully advance the catheter without the need for releasing and "resetting" the sleeve.

In particular, unlike the wide sleeves of limited flexibility that have been used on gel catheters, the very flexible, narrow sleeve on the hydrophilic catheter of the present invention can easily be moved from the insertion end toward the funnel end as the catheter tube is advanced into the urethra in a no-touch sure grip fashion because of the highly lubricious water vapor hydrated hydrophilic coating and the collapsible nature of the sleeve.

DRAWINGS

DETAILED DESCRIPTION OF THE PREFERRED EMBODIMENTS

Figure 1:
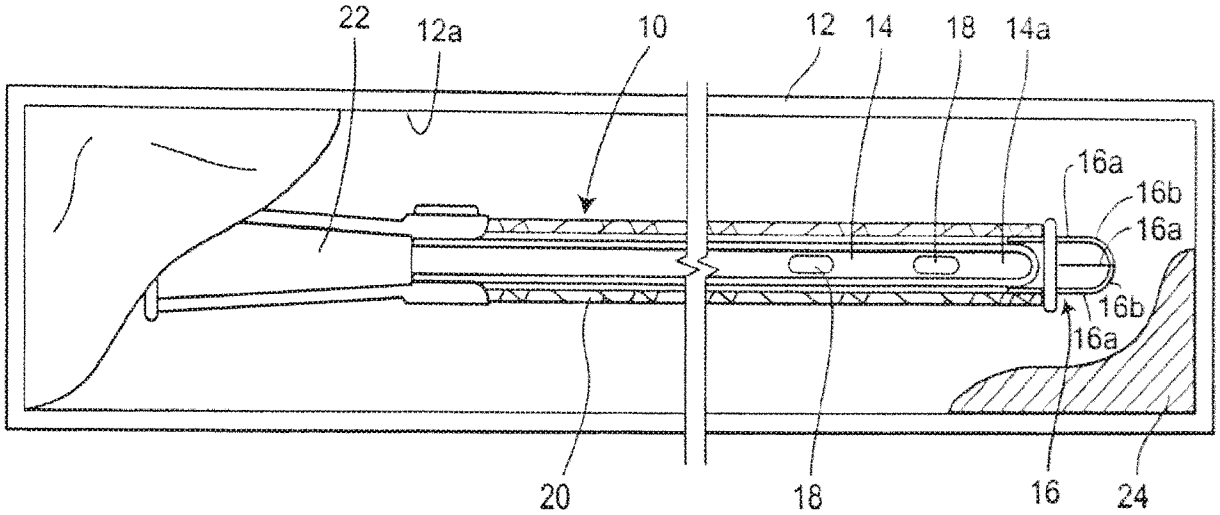
FIG. 1 is a top plan view, partially broken away, of a vapor hydrated packaged hydrophilic catheter assembly according to the present invention.

Referring to FIG. 1, the present invention comprises a hydrophilic catheter assembly 10 that is adapted for vapor hydration within the catheter package 12 so it is ready for use when it reaches the end user. The catheter package 12 is liquid and gas impermeable and may be formed of an aluminum foil. The catheter assembly 10 within the package 12 includes a catheter tube 14 having an outer surface with a hydrophilic coating on at least a portion thereof, an optional soft, rubbery introducer tip 16 adjacent an end 14a of the tube intended for pre-insertion into the urethral opening before advancement of the catheter tube, and drainage eyes 18 near the proximal insertion end 14a of the tube for draining the bladder. The catheter assembly 10 may also include a thin, flexible, collapsible sleeve 20 preferably formed of a polymeric film that is vapor permeable (although it may be liquid impermeable) and through which the hydrophilic coating can be vapor hydrated. A connector 22 in the form of a tapered funnel is located at the distal end of the catheter tube for connection by the user to a flexible drain tube leading to a urine collection device (not shown).

During manufacture, the catheter tube 14 is attached to the flannel 22 and it receives a hydrophilic coating on its outer surface. The flexible hydrogel sleeve 20 is then placed over the tube 14 and the introducer tip 16, if needed, is added to complete the catheter assembly 10. The sleeve is attached either to the funnel or to the introducer tip or port, or to both. The catheter assembly 10 is then inserted into a cavity 12a formed within and defined by the package 12, together with a small pre-determined amount of a vapor donating liquid such as water as at 24, after which the package is sealed. The presence of water within the sealed gas impermeable package 12 causes water vapor to be formed over a determinable period of time. The flexible sleeve 20, preferably of a thin, flexible hydrogel material, has a high water vapor transmission rate. Thus, the flexible hydrogel sleeve 20 permits the water vapor created by the evaporating liquid located externally of the sleeve to enter and hydrate the hydrophilic coating on the outer surface of the tube 14.

The hydrophilic coating on the outer surf ice of the tube 14 therefore becomes hydrated by reason of exposure to the water vapor. This activates the hydrophilic coating to create a highly lubricious condition on the outer surf ice of the tube 14 which places the catheter assembly 10 in ready-to-use condition. The catheter assembly is aged for a predetermined period after completion of the packaging process, to ensure complete activation of the coating. The catheter assembly can then be removed by the user from the package 12 and used immediately. Moreover, this can all be accomplished without the necessity for the user to add water and without the user encountering the prior all: problems of water spillage when the package is opened.

The sleeve 20 may be formed of any of a variety of thin, flexible polymeric film materials, such as polyethylene, plasticized PVC, or polypropylene, but elastomeric film materials such as polyurethane, and particularly elastomeric hydrogel materials, are believed particularly suitable, One such material is a polyurethane polyethylene oxide block copolymer commercially available under the trademark Medifilm 435 from Mylan Labs, St. Albans, Vt., but other elastomeric hydrogel films are known and may be used. Most desirably, the film is vapor permeable, since such vapor permeability promotes distribution of vapor within the package and facilitates vapor hydration of the catheter's hydrophilic coating. It is also preferred that the flint be impermeable to liquid water, to ensure a complete barrier to microbe penetration, although a liquid permeable sleeve may in some instances be used.

The thickness of the film from which the sleeve is formed may vary considerably depending on factors such as stretchability and flexibility of the material selected but, in general, the thickness will fall within the range of about 10 to 150 microns, preferably about 13 to 50 microns. Similarly, the aging or incubating time required to achieve full vapor hydration depends on a number of variables such as the moisture vapor transmission rate (MTVR) of the material of the sleeve, the size of the package as a whole, the diameter of the sleeve in relation to other components such as the catheter tube, and the ambient temperatures and pressures involved. In any event, the interval between packaging and use is both substantial and predetermined for any given product to ensure that the vapor donating liquid within the package has vaporized sufficiently to produce a condition of 100% humidity—with complete vapor hydration of the hydrophilic coating—by the time the catheter is required for use. At such time, the amount of vapor donating liquid left within the package should be so slight as to constitute enough to maintain a condition of 100% humidity without presenting any risk of spillage when the catheter is removed from the package at the time of use. Recognizing the variables given above, the interval between packaging and use will generally be on the order of 1 to 45 days or more.

As an alternative to aluminum foil, which is a very good water vapor barrier, other packaging materials may be chosen for other considerations, such as thermoformability or cost. It is to be understood that the term "gas impermeable" in regard to the package is a relative term. The package must be enough of a barrier to moisture vapor to maintain a 100% relative humidity condition inside the package to ensure continuous hydration of the hydrophilic coated catheter for the desired shelf life of the packaged catheter assembly. The barrier properties required for this goal will depend on the length of the desired shelf life (typically between six months and five years), the amount of vapor donating liquid placed in the package prior to sealing the package, and the conditions under which the product is stored.

Figure 1A:
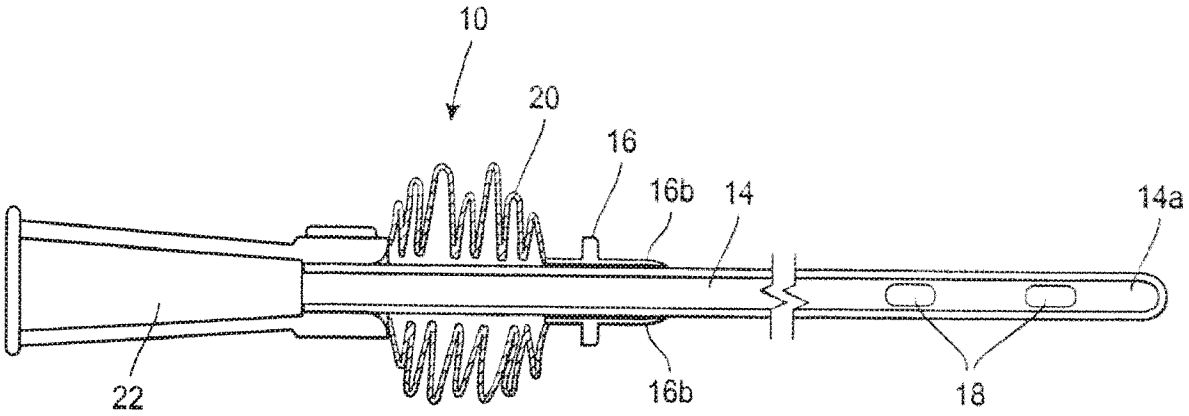
FIG. 1a is a side elevational view, partially in section, of the hydrophilic coated catheter assembly of FIG. 1 with the sleeve crumpled against the funnel.

To use the catheter assembly 10, the user may simply remove it from the package 12 by gripping the sleeve 20 and then gently insert the introducer tip 16 into the urethral opening. Preferably, the catheter assembly 10 is gripped by the sleeve 20 in one hand for advancement of the formed tip 14a of the tube 14 into and through the introducer tip 16, such introducer tip having a plurality of crossed slits 16a defining a circumferential array of flaps 16b that flex outwardly to form an opening for allowing passage of the tube 14 therethrough. Thereafter, the tube is gently advanced by using the other hand to grip the tube between wall portions of the sleeve and urge the tube forwardly or proximally. As the tube 14 advances through the urethral opening into the body, the sleeve 20 will crumple adjacent the funnel 22 of the catheter assembly 10 as shown in FIG. 1a.

Figure 2:
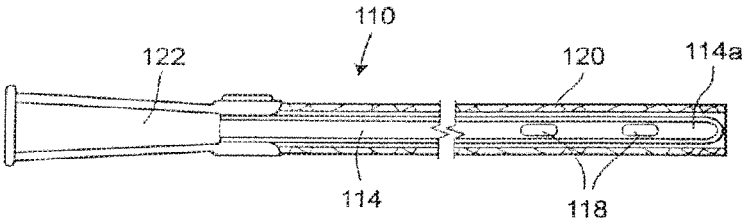
FIG. 2 is a side elevational view, partially in section, of another embodiment of hydrophilic catheter assembly according to the present invention.

Referring to FIG. 2, a catheter assembly 110 is disclosed which is quite similar to the catheter assembly 10 described above. A liquid and gas impermeable package or container, which may be similar to the package 12, encloses the assembly 110 but is omitted in FIG. 2 for clarity of illustration. As in FIG. 1, a small predetermined amount of vapor donating liquid such as water is introduced into the package, external to the catheter assembly, for vapor hydration of the hydrophilic coating during the interval following sealing of the package and prior to catheter use.

The catheter assembly 110 comprises a tube 114 having an outer surface, drainage eyes 118 for draining the bladder, and a thin, flexible sleeve 120, preferably of an elastomeric hydrogel film, through which the tube 114 can be vapor hydrated in accordance with the invention, and it may also include a funnel 122 for connection to a urine collection device. However, the principal difference in the catheter assembly 110 is the absence of the introducer tip 16 that is present in the catheter assembly 10.

In use of the catheter assembly 110 of FIG. 2, the sleeve 120 is pulled back slightly to expose the formed tip 114a of the tube 114. The formed tip 114a is then inserted into the urethral opening, and the tube 114 is advanced into the body by gripping it through the sleeve 120. As before, the sleeve 120 crumples adjacent the funnel 122 of the catheter assembly 110 similar to what is shown in FIG. 1a.

Figure 3A:
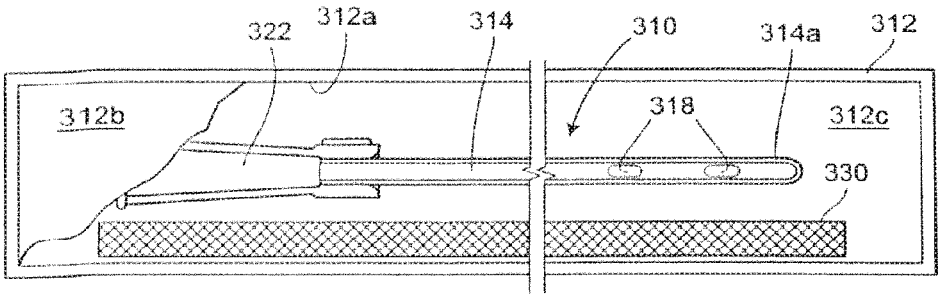
FIG. 3a is a top plan view, partially broken away, of a basic form of vapor hydrated packaged hydrophilic catheter assembly without a sleeve.

Referring to FIG. 3a, the catheter assembly 310 is a simple, less expensive arrangement similar to the catheter assembly 10 described above. The catheter assembly 310 comprises a tube 314 having an outer surface, a formed tip 314a, and drainage eyes 318 for draining the bladder, and it may also include a funnel 322 for connection to a urine collection device if required by the user. However, there are several differences that are noteworthy in relation to the catheter assembly 10 described above.

First, it will be noted that a predetermined amount of vapor donating liquid such as water can be provided within a fabric or open-cell polymeric foam liquid sequestering element 330 that may either be integrally associated with one of the walls such as 312a and 312b of a gas impermeable package 312 or may be loose within the package 312 surrounding the catheter assembly 310. The fabric or foam liquid sequestering element 330 is sized to contain an amount of water that produces sufficient, water vapor to form and maintain a 100% relative humidity atmosphere within the package 312. Since water vapor escaping from the fabric or open-cell polymeric foam liquid sequestering elements 330 is sufficient to form and maintain such an atmosphere within the package 312, the hydrophilic coating on the outer surface of the tube 314 of the catheter assembly 310 is and remains fully vapor hydrated so the catheter is ready for use.

In addition to the liquid sequestering element 330, the catheter assembly 310 will be seen to comprise a simple hydrophilic coated catheter assembly without any sleeve or introducer tip. The catheter assembly 310 is placed in the gas impermeable package 312 with a vapor donating liquid such as liquid water, and the material from which the liquid sequestering element 330 is formed is selected to have a high capillary draw to absorb all of the available liquid water to prevent any loose liquid water from being able to flow within the sealed cavity of the package 312. The liquid sequestering element is used not only to fully absorb the liquid water but also to give off water vapor after the cavity in the package 312 has been sealed to achieve vapor hydration.

Depending upon various parameters including the temperature of the liquid water placed in the package 312 and the characteristics of the hydrophilic material selected to coat the outer surface of the tube 314, vapor hydration will occur over an extended, but determinable, time period after the package has been sealed. The distribution of the packaged catheter assembly can therefore be delayed for a determinable period of time after completion of manufacture to ensure formation of a 100% relative humidity atmosphere within the package 312 and full and complete vapor hydration of the catheter. As for the liquid sequestering element 330, the material may, e.g., be a microfiber meltblown fabric, e.g., PF23100PBT manufactured by Hollingsworth & Vose Company which has been surface treated to make it liquid water wettable.

By forming the liquid sequestering element 330 of a material having a high capillary draw, the liquid water is contained in the package and not able to spill when the package is opened. This water serves as a donor to form water vapor that comprises the vapor swelling liquid for vapor hydration of the hydrophilic coating on the outer surface of the tube 314 of catheter assembly 310 after the gas impermeable package 312 holding the liquid sequestering element 330, the catheter, and the water has been sealed following manufacture. The fabric or foam material of the liquid sequestering element 330 becomes at least partially saturated with available liquid water for this purpose. Then, after the cavity in the gas impermeable package 312 has been sealed, the liquid water confined within the fabric or foam material is slowly released as water vapor until the package reaches an equilibrium state in which the air within the sealed package cavity is fully saturated with water vapor, and the water vapor is available for uptake by the hydrophilic coating on the outer surface of the tube 314 which causes the hydrophilic coating to swell so the catheter is ready for use.

Vapor hydration proceeds faster if the source of vapor is closer to the outer surface of the tube of the catheter having the hydrophilic coating thereon. It will be appreciated by referring to the embodiment of FIG. 3a as well as all of the other embodiments using a liquid sequestering element (with the exception of the embodiment of FIG. 4) that the liquid, sequestering element has been made substantially coextensive and in alignment with the length of the catheter to take advantage of this. Otherwise, vapor hydration will still occur in accordance with the invention although the time for complete hydration will be longer. If the liquid sequestering element is confined completely to one end of the package, the vapor hydration time may be considerably longer, and may become so long as to be undesirable, depending on the nature of the hydrophilic coating.

With regard to commercially available hydrophilic coatings, the time for them to become fully hydrated varies significantly. Thus, in actual testing it has been learned that one such coating was fully lubricious after two days whereas another, under the same conditions, was still not fully lubricious after two weeks. In one case, the coating was not fully lubricious until approximately six weeks miter the package was sealed.

Despite the wide diversity in time for reaching full lubricity, and the commercial desirability of reaching full lubricity in a relatively short period of time after manufacture, the advantages of the invention cart be enjoyed with any hydrophilic coating.

Figure 3B:
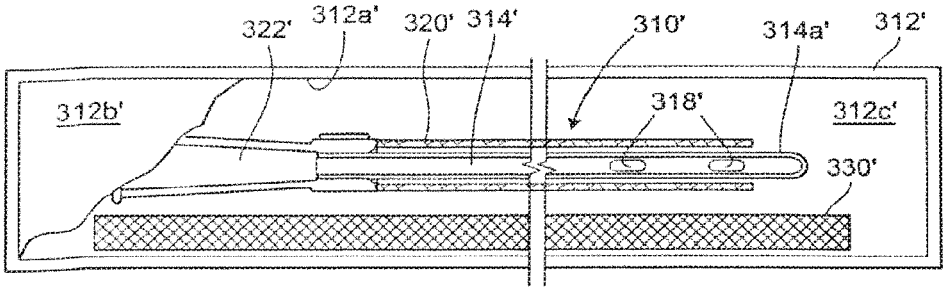
FIG. 3b is a top plan view, partially broken away, of a basic form of vapor hydrated packaged hydrophilic catheter assembly with a sleeve.

Referring to FIG. 3b, the catheter assembly 310' is an arrangement quite similar to the catheter assembly 110 described above, and it is disposed within a sealed cavity 312a' of a liquid and gas impermeable package 312' defined by the walls 312b' and 312c'. It will be seen that the catheter assembly 310' again includes a tube 314' having an outer surface and drainage eyes 318' for draining the bladder and, again, the catheter assembly 310' may include a funnel 322' which is suitable for connection to a urine collection device. Also, like the catheter assembly 110, the catheter assembly 310' includes a thin, flexible sleeve 320' preferably of an elastomeric hydrogel film through which the tube 314' can be vapor hydrated.

As with the embodiment of FIG. 3a, a predetermined amount of vapor donating liquid such as water can be provided within a fabric or open-cell polymeric foam liquid sequestering element 330' that may either be integrally associated with one of the walls such as 312a' and 312b' of a gas impermeable package 312' or may be loose within the package 312' surrounding the catheter assembly 310'. Like the liquid sequestering element 330, the fabric or foam liquid sequestering element 330' is sized to contain an amount of water that produces sufficient water vapor to form and maintain a 100% relative humidity atmosphere within the package 312'. Since water vapor escaping from the fabric or open-cell polymeric foam liquid sequestering element 330' is sufficient to form and maintain such an atmosphere within the package 312, the hydrophilic coating on the outer surface of the tube 314 of the catheter assembly 310 is and remains fully vapor hydrated so the catheter is ready for use.

Unlike the embodiment of FIG. 3a, the thin, flexible sleeve 320' is interposed between the liquid sequestering element 330' and the tube 314' of the catheter assembly 310'. It is generally known that highly flexible sleeves such as 320' which are formed of art elastomeric hydrogel film are liquid water impermeable which has meant they have generally been dismissed for use with hydrophilic coated catheters which have heretofore been hydrated by direct liquid contact.

In other words, it is water vapor hydration that makes it possible to reliably use a sleeve 320' on the catheter assembly 310'. Thus, water vapor hydration permits activation of the hydrophilic coating on the outer surface of the tube 314' of the catheter assembly 310' to ensure it is ready-to-use, unlike liquid water that could not reliably reach the coating. Since sleeves such as 320' prevent direct liquid contact with the hydrophilic coating, they have not previously been viewed as suitable for use with ready-to-use hydrophilic coated catheters.

In use of the catheter assembly 310' of FIG. 3b, the sleeve 320' is pulled back slightly to expose the formed tip 314a' of the tube 314'. The formed tip 314a' is then inserted into the urethral opening and the tube 314' is advanced into the body by gripping it through the sleeve 320'. As before, the sleeve 320' crumples adjacent the funnel 322' of the catheter assembly 310' similar to what is shown in FIG. 1a.

Figure 3C:
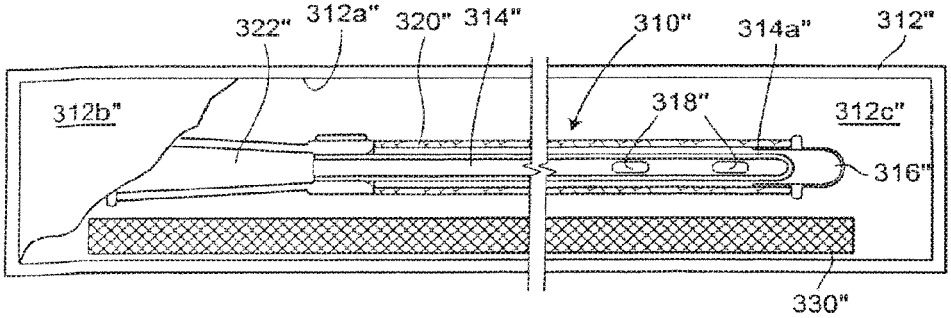
FIG. 3c is a top plan view, partially broken away, of a vapor hydrated packaged hydrophilic catheter assembly with a sleeve and introducer tip.

Referring to FIG. 3c, a catheter assembly 310" is disclosed which is also quite similar to the catheter assembly 10' described above. The catheter assembly 310" will be seen to comprise a tube 314" having an outer surface with a hydrophilic coating, a formed tip 314a", an introducer tip 316", drainage eyes 318" for draining the bladder, and a flexible sleeve 320", and it also will be seen to include a funnel 322" for connection to a urine collection device if desired. However, the principal difference in the catheter assembly 310" will be seen to be the use of a liquid sequestering element 330" within the sealed cavity 312a" of a liquid and gas impermeable package 312" defined by walls 312b" and 312c".

In the embodiment of FIG. 1, the liquid water is placed loosely within the cavity of the package 12 to create the water vapor hydrating atmosphere that will cause the hydrophilic coating on the outer surface of the tube 14 of the catheter assembly 10 to be activated. The sleeve 20 is impermeable to the loose liquid water within the sealed cavity of the package 12 but is preferably water vapor permeable. Thus, the loose liquid water forms a water vapor atmosphere within the sealed cavity of the package 12 which reaches an equilibrium condition and activates the hydrophilic coating on the outer surface of the tube 14.

In contrast, the embodiment of FIG. 3c achieves water vapor hydration of the hydrophilic coating on the outer surface of the tube 314" of the catheter assembly 310" in the manner described in connection with FIG. 3b through water vapor which is given up by the liquid water in the liquid sequestering element 330" rather than from water vapor formed from loose water as in FIG. 1.

Figure 4:
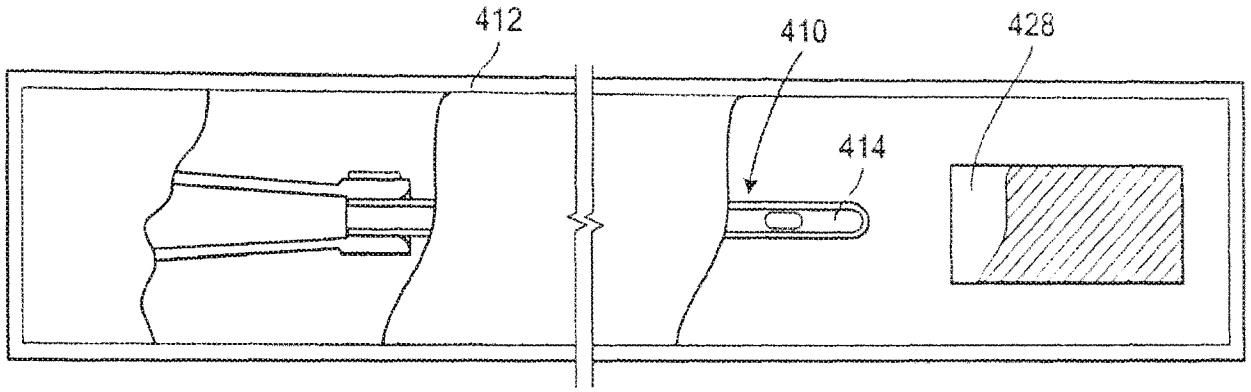
FIG. 4 is a top plan view, partially broken away, of a vapor hydrated packaged hydrophilic catheter assembly having a vapor donating liquid-containing vapor permeable, liquid impermeable pouch.

Referring to FIG. 4, another aspect of the invention is disclosed wherein the vapor donating liquid such as water is provided within a water vapor permeable but liquid impermeable pouch 428 that is placed inside a gas and liquid impermeable package 412. The catheter assembly 410 shown in the package 412 has the hydrophilic surface coating on the tube 414 completely hydrated by water vapor from the vapor permeable pouch 428 which will be sized to contain an amount of water that can produce sufficient water vapor to form a 100% relative humidity atmosphere within the package 412. In this manner, it is possible to completely activate the hydrophilic surface coating on the tube 414 with water vapor hydration rather than direct liquid water contact, and to maintain a 100% relative humidity atmosphere within the package for the desired shelf life of the product.

By way of example, the water vapor permeable pouch 428 can be sized to contain, e.g., 20 ml of water. Water can escape from the pouch in the form of water vapor that will fill the interior of the gas impermeable package 412 to cause the hydrophilic coating on the outer surface of the tube 414 of the catheter assembly 410 in the package to become fully hydrated within an easy to determine and control time period following completion of the packaging process.

Figure 5:
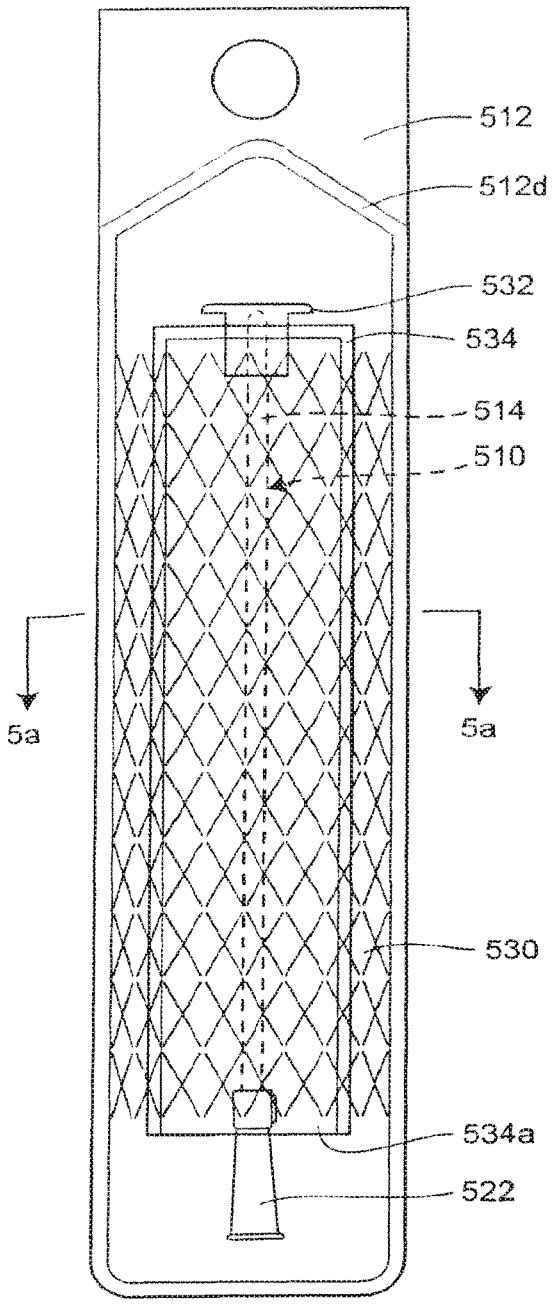
FIG. 5 is a top plan view of yet another embodiment of a vapor hydrated packaged hydrophilic catheter assembly having a catheter insertion port.
Figure 5A:
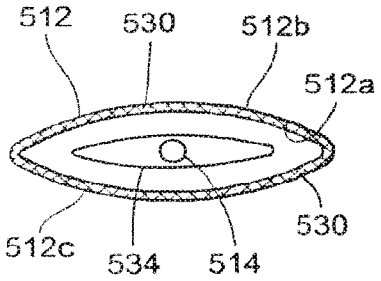
FIG. 5a is a cross-sectional view taken along the line 5a-5a of FIG. 5 illustrating the liquid sequestering material within the package.

Referring to FIGS. 5 and 5a, still another aspect of the invention is disclosed wherein a predetermined amount of a vapor donating liquid such as water is provided within a fabric or open-cell polymeric fila liquid sequestering element 530 that may either be integrally associated with the walls 512b and 512c of a gas impermeable package 512 (as shown) or may be loose within a sealed cavity 512a of the package 512 surrounding the catheter assembly 510. The catheter assembly 510 shown in the package 512 is somewhat different from earlier embodiments in that it utilizes a port 532 which, in the illustrated embodiment, takes the form of an annular guide housing located at the end opposite the funnel 522. The port has an axial passage for sliding advancement of the catheter tube 514 therethrough. However, it will be understood and appreciated that any of the various catheter assembly embodiments could be packaged in a package such as 512 that has a fabric or foam liquid sequestering element 530 contained therein. The fabric or foam liquid sequestering element 530 is sized to contain an amount of water that can produce sufficient water vapor to form and maintain a 100% relative humidity atmosphere within the package 512. Sealingly secured to the outer surface of the port 532 is a wide, thin-walled sleeve 534 extending distally therefrom to cover the catheter tube 514 substantially along its entire length into the region of the funnel 522. This wide sleeve allows the funnel to enter the sleeve as the catheter is being advanced into the body, when the catheter is being used. Water vapor escaping from the fabric or foam liquid sequestering elements 530 can fully hydrate the hydrophilic coating on the outer surface of the tube 514 of the catheter assembly 510 in order to be ready for use.

More specifically, the water vapor can fully hydrate the hydrophilic coating by passing through the sleeve 534 if it is formed of a material that has a sufficiently high water vapor transmission characteristic and/or by passing through the open end 534a of the sleeve 534 into the space between the sleeve and the catheter tube 514 whether the sleeve is vapor permeable or not.

Still referring to FIGS. 5 and 5a, it will be seen that there is a peripheral seal 512d entirely surrounding the catheter assembly 510 within the sealed cavity of the gas impermeable package 512. The port 532 makes it possible to open the package 512 at the end nearest the port 532, remove the catheter from the package, and use the port 532 to introduce the catheter tube 514 into the urethral opening. Thereafter, the user may continue the process of farther inserting the tube 514 into the body in a sterile manner by gripping it through the sleeve 534 and feeding it through the port 532 in a manner previously disclosed.

Figure 6:
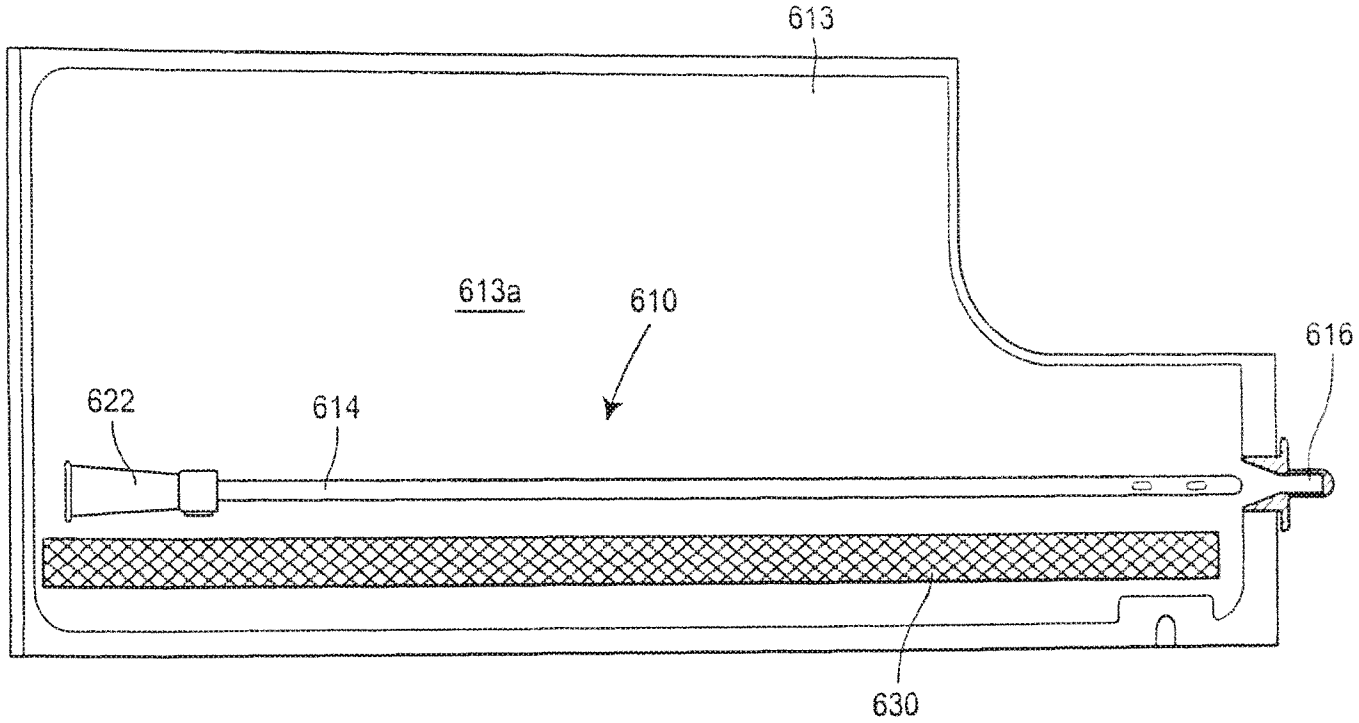
FIG. 6 is a top plan view of still another embodiment incorporating a urine collection bag in a vapor hydrated packaged hydrophilic catheter assembly.

Referring to FIG. 6, yet another aspect of the invention is disclosed wherein a predetermined volume of water is provided within a fabric or foam liquid sequestering element 630 in the form of a thin, elongated strip extending for the entire length of the catheter. The liquid sequestering element 630 may be integral with one or both of the walls such as 613a of a urine collection bag 613 that can be contained within a gas impermeable package of the types described above. The catheter assembly 610 shown in the bag 613 is similar to the embodiment of FIG. 1 in that it utilizes an introducer tip 616 at the end opposite the funnel 622 through which the catheter tube 614 can be advanced as it is introduced into the body. The fabric or foam liquid sequestering element(s) 630 may be formed of a non-sticking material such as a bicomponent fiber through air bonded fabric that has been hot calendered on one side to form a liquid permeable skin, or may be covered along their inner surfaces with a very thin film (preferably an elastomeric hydrogel film) to prevent sticking of the liquid sequestering elements on the surface of the catheter tube 614. The liquid sequestering element(s) 630 are sized to contain an amount of water that can produce sufficient water vapor to form and maintain a 100% relative humidity atmosphere within the package for the urine collection hag 613. In this manner, the water vapor escapes from the fabric or foam liquid sequestering element(s) 630 through the thin hydrogel elastomer film so that over a predetermined, time interval it can filly hydrate the hydrophilic coating on the outer surface of the tube 614 of the catheter assembly 610 in order to be ready for use.

While not shown in the drawings, it will be appreciated that embodiments of the fabric or foam liquid sequestering element where the liquid sequestering element is not integrally associated with the walls of the bag 613 are also possible.

A feature of the embodiments that utilize a vapor donating liquid such as water in a fabric or foam liquid sequestering element is that the water is not designed to be capable of hydrating the catheter by direct contact with the catheter surface. This is because the liquid sequestering element will hold the liquid water in its interstices, thus preventing loose liquid water from presenting a spill hazard. The liquid sequestering element materials are preferably fabrics or foams that are not easily compressed, which would tend to expel water from the interstices. They should be fabrics or foams that are resistant to compression so they will reliably contain the water in their interstices. preferred embodiments, the amount of water in the fabric or foam liquid sequestering element will also be not of sufficient volume to immerse the catheter, even if the water were able to escape from the liquid sequestering element. However, the fabric or foam liquid sequestering element makes it possible to use a larger volume of water in certain applications such as where it might be desired to limn the packaging of a more permeable material.

Because of the foam or fabric liquid sequestering element, the larger volume of water can be used without appreciably increasing the spill hazard even if the package is opened soon after manufacturing.

As time passes, the amount of water in the more permeable package will gradually decrease as water vapor escapes from the package which will further reduce or eliminate any possible spill hazard.

Thus, it will be appreciated that the use of liquid sequestering elements allows for inclusion of larger amounts of water in the package at the time of sealing, permitting the use of less impermeable packaging materials that may be desirable for the reasons discussed above. Embodiments that utilize a liquid sequestering element can have larger amounts of water included in the package without having any significant loose water in the package at the time of removal of the catheter from the package that would otherwise present a spill hazard at that time.

Figure 7:
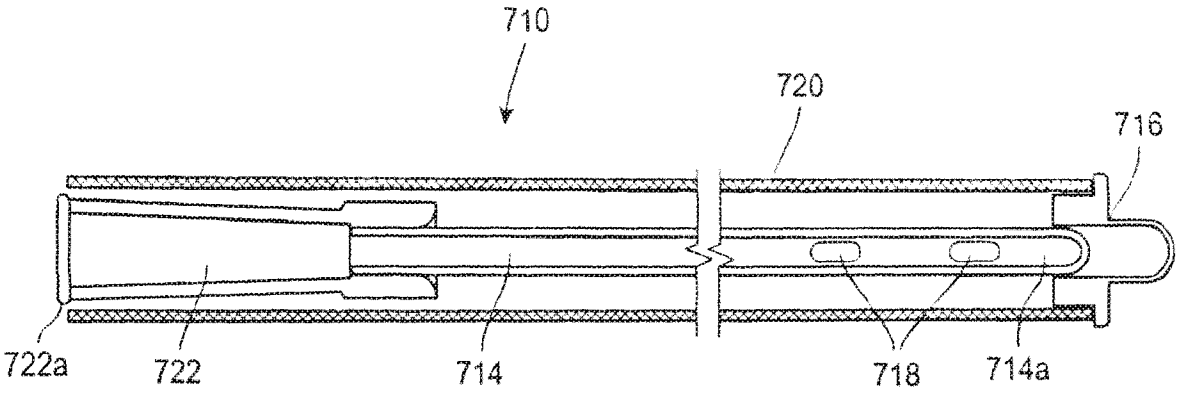
FIG. 7 is a side elevational view, partially in section, of yet another hydrophilic coated intermittent catheter assembly similar to that of FIG. 1.

Referring to FIG. 7, a catheter assembly 710 is disclosed which is also quite similar to the catheter assembly 10 described above. The catheter assembly 710 will be seen to comprise a tube 714 having an outer surface with a hydrophilic coating, an introducer tip 716, drainage eyes 718 for draining the bladder, and a flexible sleeve 720 in accordance with the invention, and it also will be seen to include a funnel 722 for connection to a urine collection device if desired. However, the principal difference m the catheter assembly 710 is the use of a wider sleeve 720 secured to the introducer tip.

To use the catheter assembly 710, the user may simply remove it from its package (not shown) by gripping the wide sleeve 720 and gently inserting the introducer tip 716 into the urethral opening. The catheter assembly 710 is gripped by the wide sleeve 720 in one hand for insertion of the formed tip 714a of the tube 714 into the urethra, and the tube 714 is gently pushed into the body using the wide sleeve 720 to advance the tube through the introducer tip 716. As the tube 714 advances through the urethral opening into the body, the wide sleeve 720 is of a sufficient size to receive the funnel 722 which may continue to advance through the sleeve until it reaches the introducer tip 716. This is an arrangement one could use When a sleeve is made from an inexpensive though relatively stiff material, like polyethylene.

Although not shown in a package, it will be appreciated that the catheter assembly 710 can be provided in a package such as any of those described above in order for vapor hydration to ensure complete activation of the hydrophilic coating on the outer surface of the tube 714 as a result of creation of a 100% relative humidity atmosphere within the package.

Figure 8:
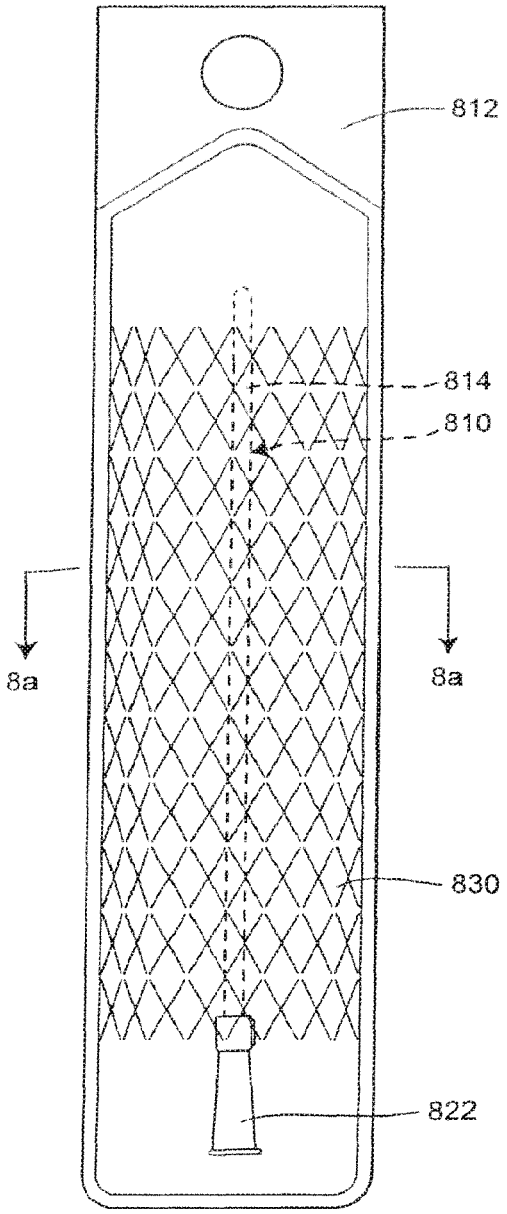
FIG. 8 is a top plan view similar to FIG. 5 of an embodiment of a hydrophilic catheter assembly without a sleeve and catheter insertion port.
Figure 8A:
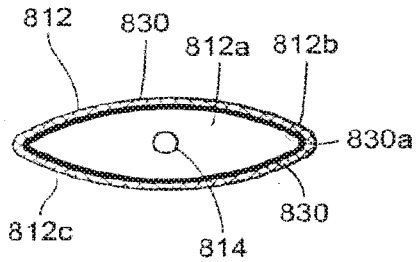
FIG. 8a is a cross-sectional view taken along the line 8a-8a of FIG. 8 illustrating the liquid sequestering material within the package.

Referring to FIGS. 8 and 8a, an embodiment similar to FIGS. 5 and 5a is disclosed wherein a predetermined amount of a vapor donating liquid such as water is provided within a fabric or open-cell polymeric foam liquid sequestering element 830 that may either be integrally associated with the walls 812b and 812c of a gas impermeable package 812 (as shown) or may be loose within a sealed cavity 812a of the package 812 surrounding the catheter assembly 810. As mentioned before, it will be understood and appreciated that any of the various catheter assembly embodiments could be packaged in a package such as 812 that has a fabric or foam liquid sequestering element 830 contained therein. The fabric or foam liquid sequestering element 830 is sized to contain an amount of water that can produce sufficient water vapor to form and maintain a 100% relative humidity atmosphere within the package 812. Water vapor escaping from the fabric or foam liquid sequestering elements 830 can fully hydrate the hydrophilic coating on the outer surface of the tube 814 of the catheter assembly 810 in order to be ready for use.

In this embodiment, the fabric or foam liquid sequestering element 830 will preferably have a thin vapor permeable film 830a on the surfaces facing the catheter assembly 810 to prevent the fabric or foam from sticking to the surfaces of the catheter assembly. More specifically, the water vapor can pass through the vapor permeable film Which is preferably formed of a hydrogel material to thereby fully hydrate the hydrophilic coating by vapor contact with the surface of the catheter tube 814.

While not specifically shown in other embodiments, the liquid sequestering elements in each of the embodiments utilizing this feature can have a film covering over the fabric or open-cell polymeric foam material to prevent the material from sticking to the coating on the catheter tube. Alternatively, the film can be replaced with a polymeric netting or a perforated plastic film. Another way to achieve the same goal is to use a fabric for the material of the liquid sequestering element that is thermally bonded through the use of binder fiber (i.e., through air bonded fabrics) which develops a liquid permeable skin during manufacture to provide a non-stick surface.

In another respect, the catheter assembly of the invention can be supplied to the user either sterile or non-sterile depending upon whether it is subjected to a known sterilization procedure.

With the present invention, there are at least two significant advancements that have been achieved for the first time by providing a hydrophilic coated catheter which is ready-for-use, highly lubricious, easy to handle, and cost effective.

The first advancement resides in providing a hydrophilic coated catheter that is hilly hydrated and ready-for-use without need for an immersion fluid that could spill when the package is opened. It has been :found, surprisingly, that this can be achieved by simply adding to the gas impermeable catheter package a small amount 01' water which is less than what would be required to immerse the catheter, and less than what could cause a spilling problem. The commercial distribution of the packaged catheter assembly is then managed in such a manner that the product will not be made available to the user prior to an adequate aging period which is determined to be sufficient i) to create a 100% relative humidity atmosphere within the package, and ii) to ensure vapor hydration of the hydrophilic coating on the outer surface of the catheter tube. By using very little water and managing commercial distribution in this manner, it is possible to provide a fully hydrated, ready-to-use hydrophilic coated catheter that will not be capable of liquid spillage when the catheter is removed from the package for use.

The second advancement resides in providing a hydrophilic coated catheter that utilizes a simple sleeve that is inexpensive to manufacture but easy to use. It has been found that simple sleeves such as those that are typical of ones that have been used on gel coated catheter products in the past show some disadvantages when they are used for hydrophilic coated intermittent catheters, However, those disadvantages are overcome by using vapor hydration to activate the hydrophilic coating in accordance with the present invention.

What has been achieved with the present invention is the advancement of providing a flexible sleeve with a fully vapor hydrated hydrophilic coated catheter that has no risk of liquid spillage by reason of prepackaging an assembly comprised of the catheter and sleeve with a small amount of vapor donating liquid following which the commercial distribution of the product is managed in a way that ensures the product will not be available to the user prior to complete hydration as the result of an adequate aging period.

The required aging period depends on whether a sleeve is used and, if so, the materials chosen for the sleeve. Inexpensive materials such as polyethylene can be used even in very thin, flexible sleeves provided the aging period is adequate. However, it has been found that the aging period which is required can be reduced by choosing sleeve materials that are more permeable to water vapor than polyethylene. For example, a water vapor permeable, but non water-swellable, elastomer film can be used which does not require as long of an aging period as does polyethylene. Furthermore, a water swellable elastomer :film which is even more permeable to water vapor can be used as a sleeve material in order to require an even shorter aging period. In general, the required aging period will be shutter for sleeve embodiments where the sleeve has higher water vapor permeability.

As will be appreciated, using a sleeve material having a greater degree of flexibility results in a sleeve that provides essentially no noticeable resistance to the advancement of the catheter, even as the sleeve is bunched against the catheter funnel during insertion. This is a significant benefit to the user of the catheter and sleeve assembly. When a very flexible sleeve material is used, there is no need to release and "reset" the sleeve during the insertion. instead, one can fully insert the catheter without releasing one's grip on the sleeve.

Test 1 below shows that in using a wide polyetheylene film sleeve with a hydrophilic coated catheter in the traditional way of adding enough water to the package to immerse the catheter, and waiting 30 seconds, complete hydration of the catheter is not achieved. Further, as shown in the table for Test 1, it has been found that use of narrower sleeves having the more desirable characteristics noted above give even worse results for hydration.

More flexible sleeves, which are capable of allowing the catheter to be inserted without resisting catheter advance as the sleeve accordions, are also useful. However, the table for Test 1 shows that as the sleeve is made of thinner material to provide a more flexible sleeve, one gets even worse results in regard to hydration. Thus, the use of a simple sleeve with a traditional hydrophilic coated catheter provided in the traditional dry format has important disadvantages.

Test 2 below shows the results of aging hydrophilic coated catheters that have narrow, flexible sleeves, and that are packaged with various small amounts of water. Amounts of water, e.g., on the order of 2 to 3 ml, can be added to the package which, after aging, results in a fully hydrated and fully lubricious catheter (a coefficient of friction of 0.03 or lower is considered indicative of full lubricity). The use of this relatively limited amount of water means the sealed package cavity containing the catheter will be almost empty, and there will be little or no loose or free liquid water remaining in the package when it is later opened for use of the catheter. Also, slightly larger amounts of water, e.g., 4 to 5 ml or even higher, can be used if the cavity is sufficiently large in volume, because the limited water left in the package at the end of aging represents such a small fraction of the overall cavity volume that it is not a significant spill hazard. Amounts of loose water should be used that occupy less than 20% of the volume of at least the tube-receiving portion of the catheter receiving cavity of the package.

In the embodiment illustrated in FIG. 1, the catheter receiving cavity is a single, large open cavity that receives the entirety of the catheter assembly 10, including not only the catheter tube 14 but also the funnel 22. Preferably, the loose water should occupy less than 10%, and most preferably less than 5% of the total volume of the tube-receiving portion of the catheter receiving cavity of the package. This contrasts With the 10 ml or more of liquid normally used for immersion of catheters, in narrow cavities that are typically filled to 45-60% of their capacity, for liquid activation, thereby presenting a definite spill hazard at the time the catheter is removed from the package for use.

Test 3 below shows that after two weeks of aging at room temperature, catheters with a polyethylene sleeve are not fully hydrated whereas those with water vapor permeable elastomer film sleeves are. These water vapor permeable elastomer films have a further advantage over polyethylene in that they have a much greater degree of flexibility which is a benefit in use of the catheter assembly. However, Test 3 shows that if a long enough aging period is used, full vapor hydration can be achieved even when a close fitting water vapor impermeable sleeve (e.g., a polyethylene sleeve) is used.

Test 4 below shows that in a given aging period, the catheter with the less permeable elastomer film sleeve (Medifilm 810) is not as fully hydrated as the catheter with the more permeable elastomer film sleeve (Medifilm 435).

Test 5 below shows that sleeves have yet another advantage when used in conjunction with vapor hydrated hydrophilic coated catheters. They reduce the rate at which the hydrated catheter will dry out as it is exposed to air when the user opens the package containing the catheter which, in turn, increases the time that the user may take to insert the catheter without the risk of a decrease in the lubricity of the catheter. It has been found that this advantage remains even for sleeves of extremely high water vapor permeability. It will also be appreciated that the more fully the catheter is hydrated on insertion the less chance for premature drying of the catheter within the body prior to removal.

Test 6 below shows the results of aging low cost catheters that do not have sleeves that are packaged with a liquid sequestering element containing vapor donating water. Depending, on the hydrophilic coating, it may take a relatively short time (2 days), or a relatively long time (more than 6 weeks) for the coating to become fully lubricious.

In the tables which accompany the tests described below, there are values set forth in some instances for the coefficient of friction. Each coefficient of fiction measurement listed in the tables was obtained as follows: Two catheters were prepared and aged in the same way. Each catheter was then cut into four or six short segments. Two short segments from a catheter were then placed in a fixture. A sled was pulled across the surface of both segments for one measurement. This was repeated in five independent trials. The average coefficient of friction is reported in the tables.

In regard to the percent filling of the tube-receiving portion of the catheter receiving cavity o fate package with hydrating liquid, it is measured as follows. First, the catheter package, as received by the user, is held in a vertical fashion with the funnel end of the catheter at the top of the package. Then, the funnel end (top) of the package is opened and peeled to the base of the funnel, where the funnel first meets the shaft of the catheter tube. The hydrating liquid that is in the package is poured out and measured, without disturbing the catheter in the package. Next, water is poured into the package to fill the entirety of the tube-receiving portion of the catheter receiving cavity of the package until the water begins to spill out. Then, the water in the tube-receiving portion of the catheter receiving cavity of the package is poured out and measured. This amount of water represents the volume of the tube-receiving portion of the catheter receiving cavity of the package.

Once the amount of hydrating liquid or vapor donating liquid that was contained in the package has been measured, and the amount of water needed to fill the tube receiving portion of the catheter receiving cavity of the package has been measured, the ratio between these two amounts should be less than 20%, to ensure against a spill hazard for the user.

The tests described below and the results derived from those tests demonstrate the advantages to be derived from the present invention.

Test 1:

In this test, dry hydrophilic catheters are immersed in water for 30 seconds including a sleeveless control catheter and catheters having sleeves. Subsequently, the catheters including the control and those with sleeves were tested for percent hydration based on wet weight versus dry weight. Commercially available hydrophilic catheters were used for this test, i.e., LoFric® catheters available from Astra Tech and EasiCath® catheters from Coloplast. The results are as follows:

| Sample Description | Weight Gain LoFric | Weight Gain EasiCath |
|---|---|---|
| Control with no sleeve | Assume 100% | Assume 100% |
| Catheter with 50 microns thick, 30 mm wide Polyethylene sleeve | 81% | 89% |
| Catheter with 50 microns thick, 8 mm wide Polyethylene sleeve | 51% | 81% |
| Catheter with 36 microns thick, 8 mm wide Polyethylene sleeve | 45% | 66% |
| Catheter with 25 microns thick, 8 mm wide Polyethylene sleeve | 35% | 58% |
| Catheter with 25 microns thick, 8 mm wide Medifilm 435 swellable elastomer sleeve | 13% | Sleeve stuck to catheter |

Test 2:

In this test, hydrophilic catheters are placed in Aluminum foil packages with from 0.5 ml to 4 ml of water added to each of the packages. The total volume of the packages is about 80 ml. The catheters are Ch 14 catheters with a 12 mm wide sleeve of Medifilm 437. They are packaged and then aged at room temperature for three weeks. They are then removed from the package and tested in order to determine the coefficient of friction (COF). Commercially available hydrophilic catheters were used for this test, i.e., Lo Fric® catheters available from Astra Tech. The results are as follows:

| Volume of Water Added (ml) | Percent of cavity fill | COF |
|---|---|---|
| 0.5 ml | 0.6% | 0.04 |
| 1.0 ml | 1.3% | 0.03 |
| 2.0 ml | 2.5% | 0.03 |
| 3.0 ml | 3.8% | 0.02 |
| 4.0 ml | 5% | 0.02 |

Test 3:

In this test, hydrophilic catheters Ch12 were fitted with 8 mm wide sleeves of different materials and packaged with 5 ml of water. The catheters were aged for either one or two weeks (Wk(s)), at either room temperature (RT) or at 40° C. and were tested for coefficient of friction (COF). Commercially available hydrophilic catheters were used for this test, i.e., Lo Fric® catheters available from Astra Tech.

In a separate experiment (results not shown), a fabric water sequestering element as opposed to a small amount of loose water was used. In this arrangement, with a Ch 14 catheter with a narrow 12 mm polyethylene sleeve, we found that after 3 weeks at 40° C., the catheters were fully activated (COF=0.02). The results are as follows:

| Sample Description | COF 1 Wk/RT | COF 2 Wks/RT | COF 1 Wk/40° C. | COF 2 Wks/ 40° C. |
|---|---|---|---|---|
| Catheter with 50 microns thick Polyethylene sleeve | tacky surface | tacky surface | 0.02 | 0.02 |
| Catheter with 51 microns thick non-swellable elastomer film (Medifilm 810) | 0.02 | 0.02 | 0.02 | 0.02 |
| Catheter with 25 microns thick swellable elastomer film (Medifilm 435) | 0.02 | 0.02 | 0.02 | 0.02 |

Test 4:

In this test, hydrophilic catheters were fitted with 8 mm wide sleeves of different materials and packaged with 2 ml of water. The catheters were then aged at room temperature for 24 hours. Commercially available hydrophilic catheters were used for this test, i.e., Lo Eric® catheters available from Astra Tech. The results are as follows:

| Sample Description | Percent Hydration (Based Upon Wet Wt. v. Dry Wt.) |
|---|---|
| Catheter with 25 microns thick swellable elastomer film (Medifilm 435) | Assume 100% |
| Catheter with 51 microns thick non-swellable elastomer film (Medifilm 810) | 67% |

Test 5:

In this test, hydrophilic catheters were packaged with 5 ml of water and then aged in an overt for 48 hours at 40 C. After aging, the catheters were removed from the package and exposed to air for a given time. If the catheters had a sleeve, the sleeve was left on for the exposure time, then pushed back to test for coefficient of friction. Commercially available hydrophilic catheters were used for this test, i.e., Lo Fric® catheters available from Astra Tech. The results are as follows:

| Sample Description | COF/2 Min. | COF/5 Min. | COF/10 Min. |
|---|---|---|---|
| Catheter with no sleeve | 0.02 | 0.04 | 0.09 |
| Catheter with Medifilm 435 Sleeve | 0.02 | 0.02 | 0.02 |
| Catheter with Medifilm 810 Sleeve | 0.02 | 0.02 | 0.02 |

Test 6:

In this test a fabric liquid sequestering element was used in vapor hydration of catheters. Two different types of commercially available Ch14 hydrophilic coated catheters were used. In some cases these catheters were fitted with close fitting sleeves of Medifilm 437, a vapor permeable thin elastomer film. Two different test systems were used. In the "Test Tube" system, catheters were placed in a sealed test tube, where they were separated front the liquid sequestering fabric by a metal screen. In this system it is impossible for the water in the fabric to contact the catheter. The second system, "Package" is a commercial type system where the catheter and the water sequestering fabric are in a sealed foil package. The results are as follows:

| Catheter used | Sleeve/ No Sleeve | Package/ Test Tube | 2 days aged COF | 1 week aged COF | 3 weeks aged COF | 6 weeks aged COF |
|---|---|---|---|---|---|---|
| LoFric | No Sleeve | Test Tube | 0.02 | 0.02 | 0.02 | ND |
| EasiCath | No Sleeve | Test Tube | 0.07 | 0.06 | 0.04 | ND |
| EasiCath | No Sleeve | Package | ND | ND | 0.04 | 0.04 |
| EasiCath | Sleeve | Package | ND | ND | 0.04 | 0.03 |

(The abbreviation ND in this table indicates the test was Not Done for the stated conditions)

In the foregoing description, the catheter embodiments have incorporated a tube, but the invention can also be enjoyed with a catheter having a shaft formed to accommodate external urine flow. Also, the various embodiments utilizing sleeves have described the sleeve as being attached to the funnel, or to the introducer tip or port, or to both. However, it will be appreciated that yet another possibility is for the sleeve to be disposed about the tube or shall in such a manner that it is not attached to the catheter. Finally, this invention allows desirable designs and design features wherein the liquid water is incapable of reliably hydrating the catheter by direct liquid contact.

It will be seen that the present invention provides a fully lubricious vapor hydrated hydrophilic coated catheter which is ready for use, provides no risk of liquid spillage, and may utilize an advantageous sleeve. The sleeve protects the catheter from finger touch and contamination, and provides a reliable, non-slip gripping surface. It also extends the time the catheter can be out of its packaging and exposed to air to thereby ensure against premature drying and loss of lubricity. The sleeve further offers essentially no resistance to the advancement of the catheter into the body as the sleeve accordions or bunches against the catheter funnel during insertion. With the present invention, a vapor hydrated hydrophilic catheter has been provided that not only achieves all of these objectives, but it does so with a product that is inexpensive to manufacture and each to use.

While in the foregoing there have been set forth preferred embodiments of the invention, the details herein given may be varied by those skilled in the all: without departing from the true spirit and scope of the appended claims.

The invention claimed is:

[1. A catheter assembly, comprising:

a package containing:

a catheter having a hydrophilic outer surface; and a pouch having an amount of vapor donating liquid therein, the pouch being comprised of a vapor permeable, liquid impermeable material.]

[2. The catheter assembly of claim 1 wherein the hydrophilic outer surface comprises a hydrophilic coating.]

[3. The catheter assembly of claim 1 wherein the package is comprised of a liquid and gas impermeable material.]

[4. The catheter assembly of claim 1 wherein vapor donating liquid comprises water.]

[5. The catheter assembly of claim 4 wherein water produces sufficient water vapor to form 100% relative humidity atmosphere within the package.]

[6. The catheter assembly of claim 4 wherein the amount of water is 20 ml.]

[7. The catheter assembly of claim 1 wherein the vapor donating liquid donates a vapor and the vapor activates at least a portion of the hydrophilic outer surface.]

[8. The catheter assembly of claim 7 Wherein the vapor donating liquid comprises water and the vapor comprises water vapor.]

[9. The catheter assembly of claim 1 wherein the pouch contains sufficient vapor donating liquid to form a fully saturated vapor atmosphere within the package to ensure continuous hydration of the hydrophilic outer surface of the catheter through the product shelf life.]

[10. A packaged ready-to-use product, comprising:

a package containing:

a product having a hydrophilic surface; and a pouch having an amount of vapor donating liquid therein, the pouch being comprised of a vapor permeable, liquid impermeable material.]

[11. The packaged product of claim 10 wherein the hydrophilic surface comprises a hydrophilic coating.]

[12. The packaged product of claim 10 wherein the package is comprised of a liquid and gas impermeable material.]

[13. The packaged product of claim 10 wherein vapor donating liquid comprises water.]

[14. The packaged product of claim 13 wherein water produces sufficient water vapor to form 100% relative humidity atmosphere within the package.]

[15. The packaged product of claim 13 wherein the amount of water is 20 ml.]

[16. The packaged product of claim 10 wherein the vapor donating liquid donates a vapor and the vapor activates at least a portion of the hydrophilic surface.]

[17. The packaged product of claim 16 wherein the vapor donating liquid comprises water and the vapor comprises water vapor.]

[18. The packaged product of claim 10 wherein the pouch contains sufficient vapor donating liquid to folly a fully saturated vapor atmosphere within the package to ensure continuous hydration of the hydrophilic surface of the product through the product shelf life.]

[19. The packaged product of claim 10 wherein the product comprises a medical product.]

*20. A ready-to-use hydrophilic urinary catheter product, comprising:*

*A package containing:*

*a liquid;*

*a hydrophilic coated urinary catheter including a catheter tube;*

*a port having a passage for advancement of the catheter therethrough; and*

*a collapsible sleeve being attached to the port.*

*21. The product of claim 20 wherein the port comprises an annular guide housing.*

*22. The product of claim 20 wherein the port includes a proximal end and a distal end and the proximal end of the port is wider than the distal end of the port.*

*23. The product of claim 20 further including a connector located at a distal end of the catheter tube.*

*24. The product of claim 23 wherein the collapsible sleeve is attached to the connector.*

*25. The product of claim 23 wherein the connector comprises a funnel.*

*26. The product of claim 20 wherein the collapsible sleeve surrounds the catheter tube to permit gripping of the catheter tube through the sleeve.*

*27. The product of claim 20 wherein the collapsible sleeve is formed of a material selected from polyethylene, PVC, polypropylene, polyurethane, and polyethylene oxide block copolymer.*

*28. A ready-to-use hydrophilic urinary catheter and package, comprising:*

*a package defining a sealed cavity;*

*an amount of liquid located in the sealed cavity;*

*a hydrophilic coated urinary catheter located in the sealed cavity, the hydrophilic coated catheter including a catheter tube having a connector associated with a distal end of the catheter tube; and*

*a port having an axial passage for sliding advancement of the hydrophilic coated catheter therethrough, a collapsible sleeve having a proximal end portion attached to the port and a distal end attached to the connector wherein the collapsible sleeve surrounds the catheter tube.*

*29. The catheter and package of claim 28 wherein the port comprises an annular guide housing.*

*30. The catheter and package of claim 28 wherein the port includes a proximal end and a distal end and the proximal end of the port is wider than the distal end of the port.*

*31. The catheter and package of claim 28 wherein the sealed cavity of the package is defined in part by a transverse seal spaced from a top edge of the package.*

*32. The catheter and package of claim 31 wherein the transverse seal has a generally arcuate shape.*

*33. The catheter and package of claim 31 wherein the transverse seal comprises opposed upwardly extending seal portions that join at an apex.*

*34. The catheter and package of claim 31 wherein the transverse seal is generally chevron shaped.*

*35. The catheter and package of claim 28 wherein the connector comprises a funnel.*

*36. A ready-to-use hydrophilic urinary catheter product, comprising:*

*a sealed package containing:*

*an amount of liquid;*

*a hydrophilic coated urinary catheter including a catheter tube having a connector being located at a distal end of the catheter tube;*

*a port having a passage for advancement of the catheter therethrough and into the urethra; and*

*a sleeve surrounding the catheter tube and being attached to the connector and to the port.*

*37. The catheter product of claim 36 wherein the port comprises an annular guide housing.*

*38. The catheter product of claim 36 wherein the port includes a proximal end and a distal end and the proximal end of the port is wider than the distal end of the port.*

*39. The catheter product of claim 36 wherein the connector comprises a funnel.*

* * * * *